United States Patent [19]

Finnerty

[11] Patent Number: 4,661,354

[45] Date of Patent: Apr. 28, 1987

[54] TOPICAL TREATMENT OF HERPES SIMPLEX WITH A ZINC SULFATE-CAMPHOR WATER SOLUTION

[76] Inventor: Edmund F. Finnerty, 215 Windsor Rd., Waban, Mass. 02168

[21] Appl. No.: 761,676

[22] Filed: Aug. 2, 1985

Related U.S. Application Data

[63] Continuation of Ser. No. 623,071, Jun. 21, 1984, abandoned, which is a continuation of Ser. No. 409,921, Aug. 20, 1982, abandoned.

[51] Int. Cl.$^4$ ............................................. A61K 33/30
[52] U.S. Cl. .................................................... 424/145
[58] Field of Search ......................................... 424/145

[56] References Cited

U.S. PATENT DOCUMENTS 411,657  9/1889  Grosbéty ............................ 424/145
3,821,370  6/1974  Tenta .................................. 424/145

FOREIGN PATENT DOCUMENTS 0000133  1/1979  European Pat. Off. ............ 424/145
0012115  6/1980  European Pat. Off. ............ 424/145
2715711  10/1978  Fed. Rep. of Germany ...... 424/145

OTHER PUBLICATIONS

Conn, Current Therapy, 1981, pp. 682–684.
The Merck Index (1976), #1734.
Facts and Comparisons, Inc., 2/82, Antiseptics and Germicides, pp. 639–640.
Chapter 29, Aqueous Preparations, pp. 347–348.

*Primary Examiner*—Albert T. Meyers
*Assistant Examiner*—John M. Kilcoyne
*Attorney, Agent, or Firm*—Pahl, Lorusso & Loud

[57] ABSTRACT

The present invention discloses a topical treatment for herpes simplex comprising a solution of 0.15-0.3% zinc sulfate in camphor water. Optionally, an anti-infective agent, such as benzalkonium chloride, may be added to the solution.

2 Claims, No Drawings

TOPICAL TREATMENT OF HERPES SIMPLEX WITH A ZINC SULFATE-CAMPHOR WATER SOLUTION

This is a continuation of U.S. Ser. No. 623,071 filed June 21, 1984, now abandoned, which in turn is a continuation of U.S. Ser. No. 409,921, filed Aug. 20, 1982, now abandoned.

BACKGROUND OF THE INVENTION

The invention relates to a treatment of herpes simplex and more particularly to a topical treatment of herpes simplex.

Herpes simplex is a virus which exists on the skin in the form of lesions. There are two types of herpes simplex: Type 1 and Type 2. Type 1 herpes are more commonly known as fever blisters and are usually caused by excessive sun, upper respiratory infections and the like. Type 2 herpes are sexually-transmittable lesions located about the genitalia. Many people cannot manufacture a sufficient amount of antibodies to the herpes simplex virus, therefore the virus resides in their ganglia, and these people suffer from recurrent herpes simplex. Due to the very high incidence of herpes simplex in the world and the devastating nature of the virus, a large number of treatments for herpes simplex have been advocated.

In early studies, beneficial results were obtained when topical applications of 0.5% and higher concentrations of zinc sulfate solution were used in the treatment of herpes simplex infections. Due to indications that zinc was effective in the treatment of herpes simplex, zinc tablets were put on the market in the mid 1970's. Unfortunately, there was only a slight absorption of these tablets through the gut and not enough zinc was distributed to the herpetic sites to do any good. Experiments in the second half of the 1970's proved that zinc was indeed effective in the treatment of herpes simplex, since they showed that zinc interfered with the multiplication of the herpes virus at a specific point. Experimental investigations in vitro showed that zinc ions irreversibly inhibited replication of herpes simplex virus Type 1 BSC-1 cells by selective inhibition of herpes simplex virus Type 1 DNA polymerase.

In "Topical treatment of recurrent herpes siplex and posttherapeutic erythema multiforme with low concentrations of zinc sulfate solution", *British Journal of Dermatology*, (1981) pp. 191–194, Brody discloses the topical use of low concentrations of zinc sulfate solution ($ZnSO_4.7H_2O$) fo recurrent herpes simplex of the skin and oral mucous membrane. Even though the Merck Index (1968) recommended 0.2–1% zinc sulfate solution for the topical treatment of herpes simplex, Brody suggests that no more than 0.025–0.05% zinc sulfate should be used for the skin as compresses and 0.01–0.025% for the mucous membrane as rinses. Brody states that the concentrations recommended in the Merck Index are too strong and cause severe irritation, an unpleasant dryness of the skin and mucous membrane, and a strong emetic reflex. These side effects are not provoked by the low concentrations of the zinc sulfate solution that Brody uses. Brody found that immediate treatment followed by weekly to monthly maintenance treatment with the low concentrations of zinc sulfate solution prevented a relapse in all patients of recurrent herpes simplex on the skin and oral mucous membrane during an observation period of 16–23 months.

Although there have been many proposed treatments for herpes simplex which employ zinc, none of these treatments have been able to stop the itching, burning, and stinging symptoms associated with the virus in 24 hours or less, clear the lesions in approximately 5 days, and at the same time, cause no unpleasant side effects.

SUMMARY OF THE INVENTION

The problems of the prior art are overcome by the discovery of a topical treatment of herpes simplex comprising a solution of zinc sulfate in camphor water. The concentration of zinc sulfate that may be used in the camphor water solution ranges from 0.15–0.3% and is preferably 0.25%. Optionally, an anti-infective agent may be added to the zinc sulfate-camphor water solution and this anti-infective agent preferably comprises benzalkonium chloride. The concentration of this anti-infective agent in the solution may range from 0.005–0.015%, and is preferably 0.01%.

DESCRIPTION OF THE PREFERRED EMBODIMENT

At the outset the invention is described in its broadest overall aspects with a more detailed description following.

The solution of the present invention comprises between 0.15–0.3% zinc sulfate in camphor water. As used throughout this specification and claims, all percentages are by weight unless specified otherwise. As used throughout this specification and claims, camphor water is a saturated solution (about 2%) of camphor ($C_{10}H_{16}O$) in purified water. Although camphor is only slightly soluble in water, camphor water may be prepared by distillation, by simple solution in cold water, or by solution with the aid of a distributing agent. At this point it should be noted that camphor water is a standard pharmaceutical item.

To prepare the solution of the present invention, zinc sulfate is dissolved in distilled water in equivalents of 150 milligrams of zinc sulfate in 5 cc. of distilled water and then filtered through standard filter paper. Five cc. of this solution is then added to approximately 55 cc. of camphor water to give a 0.25% solution. Zinc sulfate may also be dissolved directly in camphor water. The preferred concentration of zinc sulfate in the camphor water solution is 0.25%. Optionally, an anti-infective agent may be added to the zinc sulfate-camphor water solution and the preferred anti-infective agent to be added is benzalkonium chloride. The concentration of benzalkonium chloride in the solution may range from 0.005 to 0.015%, and is preferably 0.01%.

The zinc sulfate-camphor water solution is applied directly to the herpetic sites. The solution is usually applied between 4 and 8 times daily, and is preferably applied 6 times daily. Within 24 hours after the beginning of treatment with the zinc sulfate-camphor water solution, all of the itching, burning and stinging symptoms associated with the herpes simplex virus disappear. The herpes lesions begin to dry and crust within a 24–48 hour period. The crusts formed fall off generally within 3–5 days after the start of the treatment with the zinc sulfate-camphor water solution. The invention is further illustrated by the following non-limiting example.

EXAMPLE 1

A patient was diagnosed as having acute herpes simplex on the right medial malar cheek, the right lateral upper lip, and the middle of the right vermillon border of the right upper and lower lip. The patient had active vessicular lesions on all the above-mentioned sites. The patient applied a solution of 0.25% zinc sulfate in camphor water 6 times daily to the herpetic site with a cotton swab. Any suitable means for applying the solution to the herpetic site may be used. The patient's itching disappeared with the second application of the solution and the acute vesicles were definitely drying within 6 hours of the first application. The lesions on the lip were dry and crusted within 24 hours of the first application and the lesions on the right lateral upper lip and right malar cheek were dry and crusted within 40 hours of the first application. The crusts rapidly fell off within the next 24 hours and only traces of crusting remained. All traces of the crusting then disappeared within the next 24 hours.

I claim:

1. A solution for the topical treatment of Herpes Simplex Type I comprising 0.25% zinc sulfate in camphor water.

2. A process for the topical treatment of Herpes Simplex Type I lesion or lesions comprising applying a solution comprising 0.25% zinc sulfate in camphor water to the herpetic lesion or lesions.

* * * * *